United States Patent [19]

Jefferis et al.

[11] Patent Number: 4,618,589
[45] Date of Patent: Oct. 21, 1986

[54] IMMUNOPRECIPITATION ASSAY OF IMMUNOGLOBULINS USING MONOCLONAL ANTIBODIES

[75] Inventors: Royston Jefferis, Birmingham, England; Jens Steensgaard, Aarhus, Denmark

[73] Assignee: The University of Birmingham, Birmingham, England

[21] Appl. No.: 745,837

[22] Filed: Jun. 19, 1985

Related U.S. Application Data

[63] Continuation of Ser. No. 582,155, Feb. 24, 1984, abandoned, which is a continuation of Ser. No. 351,444, Feb. 23, 1982, abandoned.

[30] Foreign Application Priority Data

Jul. 16, 1980 [GB] United Kingdom ................ 8023151

[51] Int. Cl.$^4$ ................ G01N 33/541; G01N 33/577
[52] U.S. Cl. .................... 436/540; 436/539; 436/548; 436/815; 435/68; 435/172.2; 935/110
[58] Field of Search ................ 435/7, 68, 172.2, 240; 436/513, 536-540, 548, 815, 512, 506, 507, 824, 805; 935/108, 110; 356/39, 319, 339

[56] References Cited

U.S. PATENT DOCUMENTS

| | | | |
|---|---|---|---|
| 4,236,893 | 12/1980 | Rice | 436/513 |
| 4,273,756 | 6/1981 | Ling et al. | 436/513 |
| 4,292,403 | 9/1981 | Duermeyer | 436/513 |
| 4,343,896 | 8/1982 | Wolters et al. | 436/540 |
| 4,349,528 | 9/1982 | Koprowski et al. | 424/1 |
| 4,350,683 | 9/1982 | Galfre et al. | 424/85 |
| 4,376,110 | 3/1983 | David et al. | 436/513 |

FOREIGN PATENT DOCUMENTS

| | | | |
|---|---|---|---|
| 2615092 | 10/1976 | Fed. Rep. of Germany | 436/513 |
| 2074727 | 11/1981 | United Kingdom | 435/7 |

OTHER PUBLICATIONS

Gerhard, W. et al, Proc. Natl. Acad. Sci., U.S.A., vol. 75, (3), pp. 1510-1514 (3-1978).
Yeh, M. Y. et al, Proc. Natl. Acad. Sci., U.S.A., vol. 76, (6), pp. 2927-2931 (6-1979).
McMichael, A. et al, European J. Immunology, vol. 9, pp. 205-210 (1979).
Frankel, M. E. et al, Molecular Immunology, vol. 16, pp. 101-106 (1979).
Jefferis et al, J. Immunological Methods, vol. 39(4) (1980) pp. 355-362.
Steensgaard et al, Molecular Immunology, vol. 17, p. 1315 (1980).
Deverill et al, Clinical Chemistry, vol. 27(12), pp. 2044-2047 (12-1981).
Partridge et al, J. Immunology, vol. 128(1), pp. 1-6 (1-1982).
Lowe et al, Immunology, vol. 42(4) pp. 649-659 (4-1981).

Primary Examiner—Charles F. Warren
Assistant Examiner—Margaret Moskowitz
Attorney, Agent, or Firm—Leydig, Voit & Mayer

[57] ABSTRACT

An antigen/antibody precipitate is obtained, using monoclonal antibodies, the monoclonal antibodies (samples I or II or III or IV) being selected so as to be specific to two distinct antigenic binding sites (L or C 2 or C 3) on a protein (IgG) in a sample under test. The proportions of sub-populations of immunoglobulins (IgG kappa, IgG lambda) in a sample is determined by reacting the sample with a combination of antibodies (II and IV) both of which are specific to the heavy chains (H) of both sub-populations (IgG kappa, IgG lambda) and reacting the sample with an antibody combination (I and II) specific to said heavy chain (H) and to an antigenic determinant expressed by only one (IgG kappa) of the sub-populations.

6 Claims, 3 Drawing Figures

IMMUNOPRECIPITATION ASSAY OF IMMUNOGLOBULINS USING MONOCLONAL ANTIBODIES

This application is a continuation of application Ser. No. 582,155, filed 2-24-84, abandoned, which is a continuation of application Ser. No. 351,444 filed 2-23-82 abandoned.

TECHNICAL FIELD

This invention relates to methods of immuno-analysis using monoclonal antibodies. Specific antisera are widely applied to the detection and quantitation of a target antigen when it is present in a complex mixture of molecules, and many quantitative methods depend upon precipitation resulting from the formation of insoluble antigen/antibody complexes. In the early stages of antigen/antibody interaction, the insoluble complexes are of relatively small size and are held in suspension. Several techniques of specific protein determination depend upon the light scattering or absorption properties of such complexes. One such, automated, method is based on difference turbidimetric measurements resulting from the increased (apparent) absorption properties of such complexes, held in suspension when a polyclonal antibody interacts with a multivalent antigen.

BACKGROUND ART

In 1975 Kohler and Milstein (Nature, 256, pp 495–497) reported a method of producing monoclonal antibodies directed against a single antigenic determinant. Amongst the advantages of monoclonal antibodies are (1) their unique specificity and (2) their potential to allow the development of perpetually reproducible standard reagents. However, since monoclonal antibodies are specific to a single determinant, or interaction with antigen they can only form soluble linear complexes, rather than cross-linked complexes which might be insoluble (precipitating). Therefore, individual monoclonal antibodies have not hitherto appeared to be applicable to techniques that are dependent on the formation of insoluble immune complexes.

It is an object of the present invention to provide a method by means of which monoclonal antibodies may be reacted with proteins to produce insoluble antigen/antibody complexes that will allow the application of monoclonal antibodies to techniques which require formation of the aforesaid insoluble complexes.

It is a particular object to provide a method by means of which monoclonal antibodies may be used to assay the total immunoglobulin population or selected immunoglobulin sub-populations present in complex mixtures viz. serum or other body fluids.

DISCLOSURE OF THE INVENTION

According to the invention a method of determining the amount of a particular protein in a sample comprises reacting the sample with a combination of two monoclonal antibody preparations which are respectively specific of two distinct antigenic sites (determinants) on the macromolecule of the protein under investigation, and determining from the resulting antigen/antibody complexes formed a quantitative measure of the original protein concentration.

In a particular embodiment of the method the aforesaid two monoclonal antibodies are selected so as to be specifically directed against relatively widely spaced antigenic determinants present on a given macromolecule, whereby the binding of one monoclonal antibody to its specific antigenic determinant does not interfere, spatially, with the binding of the second monoclonal antibody to the antigenic determinant for which said second antibody has specificity.

In a further particular embodiment the macromolecule comprises an immunoglobulin and the monoclonal antibodies are selected so as to be specific to antigenic determinants expressed by the light and heavy chains respectively of the immunoglobulin.

In yet another embodiment the method comprises (a) reacting a first sample including first and second immunoglobulin sub-populations with a combination of first and second monoclonal antibody preparations, both of which are specific to distinct antigenic determinants or sites that are common to both of the first and second sub-populations, that is expressed on the heavy chains of both immunoglobulins, to obtain a first antigen-antibody precipitate and determining from the resulting complex the total immunoglobulin level in the sample (b) reacting a second sample identical to the first sample with a combination of the first monoclonal antibody and a third monoclonal antibody which is specific for an antigenic determinant or site expressed by only one of said immunoglobulin, sub-population to obtain a second antigen-antibody precipitate, and (c) determining from the resulting complex the quantity of said first immunoglobulin sub-population.

There will now be described by way of example only and with reference to the accompanying drawings, procedures incorporating the methods of the invention.

BEST MODE OF CARRYING OUT THE INVENTION

Figure 1:
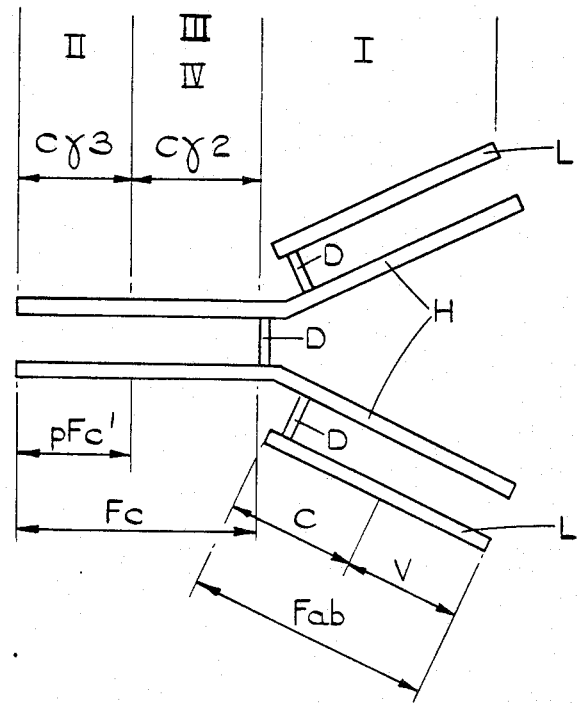
FIG. 1 is a representation of an IgG molecule, indicating the regions against which test antibodies were directed.

FIG. 1 represents a macromolecule of immunoglobulin G (IgG) having two "heavy" polypeptide chains H and two "light" polypeptide chains L, the chains H and L being linked by disulphide bonds. The molecule is symmetrical and has two antigen binding fragments Fab, each of which includes a light chain L and a portion of the heavy chain H. A crystalisable fragment Fc of both heavy chains H comprises $C\gamma2$ and $C\gamma3$ regions of equal lengths. The fragment Fc may be separated from the remainder of the molecule by enzyme action, and this fragment Fc may be subjected to a further enzyme action to leave a residual fragment pFc' whose extent is effectively that of the $C\gamma3$ region. Each chain in the Fab fragment has a variable region V and a constant region C.

Normal human IgG includes sub-populations of IgG kappa and IgG lambda, the kappa and lambda characteristics being defined by the structures of the constant regions C of the molecules.

In the examples described antibodies were elicited using polyclonal human IgG as an immunogen, and the antibody products were selected on the basis of their ability to agglutinate sheep red blood cells sensitised with human IgG. The specificity of the cloned antibody products was further defined by their ability to agglutinate sheep red blood cells sensitised with kappa light chain, lambda light chain, Fc fragments, or pFc' fragments. By these methods monoclonal antibodies were selected having specificities as indicated below;

| Sample. | Specificity. |
|---|---|
| I | Kappa light chain. |
| II | |
| III | Fc |
| IV | |

Sample II was also found to agglutinate cells sensitised with pFc' fragments, and this sample was thus directed against an antigenic determinant in the Cγ3 region of the IgG molecule. In the absence of agglutination of pFc' sensitised cells by samples III and IV, these samples were presumed to be specific to antigenic determinants in the Cγ2 region of the IgG molecule, or to be conformational determinants dependent on the structural integrity of the Fc fragment of the molecule for expression.

The antigen with which the foregoing antibodies were reacted with an IgG kappa paraprotein.

Preparations of the antibody samples I to IV were reacted with the antigen, separately and in combinations of antibody. The reactions were carried out at 25° C. in phosphate buffered solutions containing 4% polyethylene glycol (MW. 3000). The difference in turbidity of the fluid in which the reactions were performed was determined using light of wavelength 260 nm, (Jacobsen and Steensgaard, Immunology, 36 (1979) at 293-298).

Figure 2:
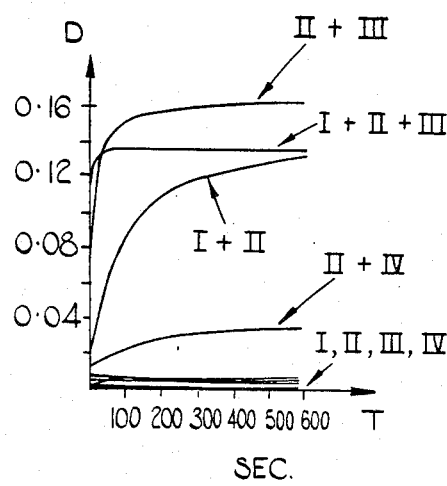
FIG. 2 is a graph of turbidity against time, for several antigen/antibody reactions.

As shown in FIG. 2, monoclonal antibody samples I to IV were reacted separately against the antigen without a significant turbidity difference, D, when plotted against a time T of up to 600 seconds. However, a combination of antibody samples II and IV produced a measurable turbidity change, while reactions with a combination of samples I and II and a combination of samples II and III provided reactions which were equivalent to that normally obtainable in reactions using polyclonal antibody reagents.

It will be seen from FIG. 2 that a reaction with a combination of samples I, II and III resulted in a turbidity difference less than that obtained with the combination of samples II and III. This result is probably due to antibody excess in the reaction.

Figure 3:
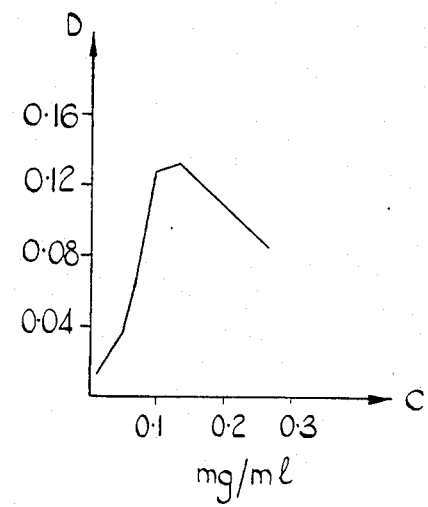
FIG. 3 is a graph of change in turbidity obtained from antigen/antibody reactions with varying antibody concentrations.

FIG. 3 shows the turbidity differences, D, obtained for a number of values of antigen concentration, C, expressed in mg/ml. The curve shown was obtained by titration of the IgG kappa paraprotein, at differenting concentrations, against a standard concentration of an antibody preparation. The antibodies used in this case where those from samples I and II, that is those directed against the spatially distinct kappa light chain and Cγ3 region of the antigen.

As indicated above the IgG content of human serum is made up of sub-populations of IgG kappa and IgG lambda. In normal serum the ratio of IgG kappa to IgG lambda lies between 3:1 and 1:1, a typical ratio being approximately 1.8:1. A significant departure from this range of ratios may indicate an early stage of myeloma, which otherwise may develop for up to twenty years before showing symptoms. Since detection and treatment at an early stage may significantly prolong life expectancy, it is clearly advantageous that the quantities of the above sub-populations should be capable of being determined.

Monoclonal antibody preparations have been used to determine the relative proportions of sub-populations of immunoglobulins present in such polyclonal IgG. For example, a test sample including IgG kappa and IgG lambda which is reacted with antibodies from sample II and sample III, both of which are directed against the Fc portion of the IgC molecule, allows quantitation of the total IgG content of the test sample. An additional IgG test sample reacted with a combination of antibodies from samples I and II will allow quantitation of the IgG kappa content. Similarly an identical IgG test sample reacted with, for example, an antibody preparation from sample II in combination with a further monoclonal antibody preparation which is specific to IgG lambda light chain will allow quantitation of the IgG lambda content. It has been found that the sum of quantitation of IgG kappa and IgG lambda carried out as above, have a high correspondence with the quantitation of total IgG content.

We claim:

1. A method for quantification of a sub-population of an immunoglobulin having first and second sub-populations, said method comprising the steps of:
   (a) reacting a first sample containing said immunoglobulin with first and second monoclonal antibody preparations which specifically bind to respective distinct antigenic sites on the macromolecule of said immunoglobulin, such that binding of one monoclonal antibody to its specific antigenic site does not intefere with the binding of the other antibody to its specific antigenic site, both of said sites being common to both of said first and second sub-populations, to obtain a first antigen-antibody precipitate;
   (b) reacting a second sample identical to said first sample with said first preparation and with a third monoclonal antibody preparation which specifically binds to an antigenic site expressed by only one of said first and second sub-populations, to obtain a second antigen-antibody precipitate; and
   (c) determining from said second antigen-antibody precipitate the quantity of said first sub-population in the sample.

2. In a method of determining the amount of an immunoglobulin in a sample, which comprises reacting the sample with antibodies specific to antigenic sites on a macromolecule of the immunoglobulin and obtaining antigen-antibody precipitates, the improvement wherein said antibodies comprise two monoclonal antibody preparations which specifically bind to respective, spatially distinct antigenic sites on said macromolecule, such that binding of one monoclonal antibody preparation to its specific antigenic site does not interfere with the binding of the other antibody preparation to its specific antigenic site, both of said sites being common to all sub-populations of the immunoglobulin.

3. A method as claimed in claim 2 in which said two antigenic sites are in the light chain and Cγ2 regions of the immunoglobulin.

4. A method as claimed in claim 2 wherein said two antigenic sites are in the light chain and Cγ3 regions of the immunoglobulin.

5. A method as claimed in claim 2 in which said two monoclonal antibody preparations specifically bind to antigenic sites expressed by the light and heavy chains respectively of the macromolecule of the immunoglobulin.

6. A method as claimed in claim 1 wherein said sub-populations of the immunoglobulin comprise IgG kappa and IgG lambda, respectively.

* * * * *